United States Patent
Lagrange et al.

(10) Patent No.: US 7,175,672 B2
(45) Date of Patent: Feb. 13, 2007

(54) COMPOSITION FOR DYEING KERATINOUS FIBERS COMPRISING AT LEAST ONE AZODIAZINE DIRECT DYE AMINATED AT THE 7-POSITION AND PROCESS FOR DYEING

(75) Inventors: Alain Lagrange, Coupvray (FR); Frédéric Guerin, Paris (FR); Sylvain Kravtchenko, Asnières (FR)

(73) Assignee: L'Oreal, Paris (FR)

( * ) Notice: Subject to any disclaimer, the term of this patent is extended or adjusted under 35 U.S.C. 154(b) by 378 days.

(21) Appl. No.: 10/902,088

(22) Filed: Jul. 30, 2004

(65) Prior Publication Data

US 2005/0108833 A1 May 26, 2005

Related U.S. Application Data

(60) Provisional application No. 60/509,945, filed on Oct. 10, 2003.

(30) Foreign Application Priority Data

Jul. 30, 2003 (FR) .................................. 03 50386

(51) Int. Cl.
*A61K 7/13* (2006.01)
(52) U.S. Cl. ........................ 8/405; 8/406; 8/407; 8/409; 8/410; 8/411; 8/412; 8/421; 8/425; 8/657; 8/689; 544/249

(58) Field of Classification Search .................... 8/405, 8/406, 407, 409, 410, 411, 412, 421, 425, 8/657, 689; 544/249
See application file for complete search history.

(56) References Cited

U.S. PATENT DOCUMENTS 2,528,378 A 10/1950 Mannheimer
2,781,354 A 2/1957 Mannheimer

FOREIGN PATENT DOCUMENTS

| DE | 197 46 137 A1 * | 4/1999 |
| EP | 1 166 754 A2 | 1/2002 |
| FR | 1 285 848 | 5/1960 |

OTHER PUBLICATIONS

English abstract of DE 197 46 137 A1.*
STIC Search Report dated Aug. 3, 2006.*
English language abstract of DE 197 46 137 A1, Apr. 22, 1999.

* cited by examiner

*Primary Examiner*—Eisa Elhilo
(74) *Attorney, Agent, or Firm*—Finnegan, Henderson, Farabow, Garrett & Dunner

(57) ABSTRACT

The present disclosure relates to a composition for dyeing keratinous fibers, comprising at least one azodiazine direct dye aminated at the 7-position. The present disclosure also relates to a process for dyeing keratinous fibers using the direct dyes described herein.

34 Claims, No Drawings

COMPOSITION FOR DYEING KERATINOUS FIBERS COMPRISING AT LEAST ONE AZODIAZINE DIRECT DYE AMINATED AT THE 7-POSITION AND PROCESS FOR DYEING

This application claims benefit of U.S. Provisional Application No. 60/509,945, filed Oct. 10, 2003.

The present disclosure relates to compositions for dyeing keratinous fibers, for instance human keratinous fibers such as hair, comprising at least one direct dye of the azodiazine compound family. It also relates to the use of compounds of the azodiazine family as direct dyes in compositions for dyeing keratinous fibers. Finally, the present disclosure relates to methods for dyeing keratinous fibers using such compositions.

To dye keratinous fibers, such as the hair, it is known to use dyeing compositions containing oxidation dye precursors, also called "oxidation bases," and optionally couplers, for instance, meta-phenylenediamines, meta-aminophenols and meta-diphenols, also called color modifiers. Oxidation dye precursors are colorless or faintly colored precursors which, when combined with oxidizing products (such as hydrogen peroxide) give rise, through an oxidation process, to colored and dyeing compounds.

However, methods for oxidation dyeing can have the following disadvantages:

because of the use of oxidizing products such as hydrogen peroxide, they can cause degradation of the keratinous fiber and a bothersome irritation of the scalp;

they can generate a fast color of the fibers, which may change over time and they often cause selectivity in the color of the fiber, that is to say, differences in color along the same keratinous fiber.

To prevent some or all of the abovementioned disadvantages, it has been proposed to return to methods of direct dyeing through the use of direct dyes, which comprises dyeing the hair by causing a colored molecule (the direct dye) to penetrate, by diffusion, into the hair without necessitating the use of hydrogen peroxide.

However, such direct dyeing methods have proven to be, up until now, unsatisfactory for instance, for the following reasons:

they can cause insufficient color fastness, wherein color fades after a few shampooings;

they too can cause selectivity in the color of the fibers, that is to say differences in color along the same keratinous fiber.

A true need therefore exists for a composition for dyeing keratinous fibers, which can be not very selective, which can give a large variety of colors, intense colors and/or which additionally can make it possible to give a fast fiber color that changes little over time.

Accordingly, the present disclosure relates to azodiazine compounds incorporated in compositions for dyeing keratinous fibers that make it possible to overcome some or all of the disadvantages that can be encountered with the prior art, and make it possible for example, to obtain a range of highly varied colors with a low selectivity, and also a good level of fastness.

For example, one aspect of the present disclosure is a composition for dyeing keratinous fibers comprising at least one dye chosen from the compounds of formula (I):

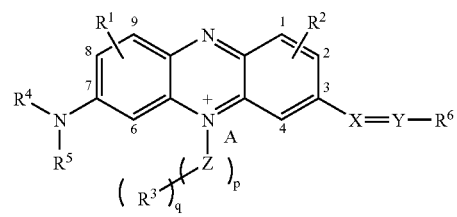

wherein:

$R^1$ and $R^2$, which may be identical or different, are chosen from:

hydrogen atoms;

alkyl groups comprising from 1 to 6 carbon atoms, it being possible for the alkyl group to be optionally substituted with at least one entity chosen from hydroxyl radicals, amino radicals, halogens, aryl radicals, and alkoxy radicals comprising from 1 to 3 carbon atoms;

aryl groups comprising from 6 to 18 carbon atoms, it being possible for the aryl group to be optionally substituted with at least one radical chosen from amino radicals, hydroxyl radicals, alkoxy radicals comprising from 1 to 3 carbon atoms, and alkyl groups comprising from 1 to 6 carbon atoms;

carboxyalkyl radicals comprising from 1 to 6 carbon atoms; and sulphoalkyl radicals comprising from 1 to 6 carbon atoms;

p is equal to 0 or 1;

when p is equal to 0, q is equal to 1, and Z is a single bond;

when p is equal to 1, Z is an alkylene radical comprising from 1 to 4 carbon atoms, the alkylene radical is substituted with q $R^3$ radicals, which may be identical or different, wherein q is an integer ranging from 1 to 5;

$R^3$ is chosen from mono- and polycyclic radicals comprising from 5 to 100 carbon atoms, which is optionally aromatic, optionally comprising at least one heteroatom and optionally at least one unsaturation, it being possible for the mono- and polycyclic radicals to be substituted with at least one entity chosen from hydroxyl radicals, cyano radicals, halogens, amino radicals, alkoxy radicals and alkyl radicals comprising from 1 to 4 carbon atoms, with the proviso that when p is equal to 0, then $R^3$ is not an aryl group;

$R^6$ is chosen from mono- and polycyclic radicals comprising from 5 to 100 carbon atoms and optionally at least one heteroatoms and optionally at least one unsaturation, it being possible for the mono- and polycyclic groups to be substituted with at least one entity chosen from hydroxyl radicals, cyano radicals, halogens, amino radicals, aryl radicals, alkoxy radicals and alkyl radicals comprising from 1 to 4 carbon atoms;

$R^4$ and $R^5$, which may be identical or different, are chosen from hydrogen atoms, and aryl and alkyl radicals comprising from 1 to 6 carbon atoms, the radicals being optionally substituted with at least one entity chosen from hydroxyl radicals, cyano radicals, halogens, amino radicals, aryl radicals, and alkoxy radicals comprising from 1 to 4 carbon atoms;

X and Y, which may be identical or different, are chosen from nitrogen atoms and CR' radicals, wherein R' is chosen from a hydrogen atom and alkyl radicals comprising from 1 to 6 carbon atoms;

A is an anionic counterion.

As used herein, the expression "alkyl radical" is understood to mean a linear or branched alkyl radical of 1 to 6 carbon atoms, for example a methyl, ethyl, n-propyl, i-propyl, n-butyl, i-butyl or t-butyl radical.

The expression "alkylene radical" is understood to mean, as used herein, a divalent alkyl group that forms a bridge between the positively charged nitrogen atom and $R^3$. By way of examples of alkylene radicals, non-limiting mention may be made of methylene radicals —$CH_2$—, and ethylene radicals —$CH_2$—$CH_2$—.

The expression "alkoxy radical" is understood to mean, as used herein, an —O-alkyl radical, the term alkyl corresponding to the same definition as that given above.

The expression "amino radical" is understood to mean, as used herein, —$NH_2$ radicals, optionally substituted on the nitrogen atom with at least one substituent such as alkyl radicals comprising from 1 to 6 carbon atoms.

The expression "aryl radical" is understood to mean, as used herein, a monocyclic or polycyclic hydrocarbon aromatic radical comprising from 6 to 18 carbon atoms, such as phenyl radicals and naphthyl radicals. The aryl radicals may be optionally substituted with radicals chosen from amino radicals, hydroxyl radicals, C1 to C3 alkoxy radicals and C1 to C6 alkyl radicals. Examples of substituted aryl groups include, for example the 2-tolyl, 3-tolyl and 4-tolyl radicals.

The expression "carboxyalkyl radical" is understood to mean, as used herein, an alkyl radical as defined above, comprising at the end a —$CO_2H$ radical, such as the carboxymethyl radical —$CH_2$—$CO_2H$ and the carboxyethyl radical —$(CH_2)_2$—$CO_2H$.

The expression "sulphoalkyl radical" is understood to mean, as used herein, an alkyl radical as defined above, comprising a sulfur atom forming a bridge between the abovementioned alkyl radical and the tricyclic unit of the compounds of formula (I).

The expression "anionic counterion" is understood to mean, according to the present disclosure, an anion capable of neutralizing the positive charge carried by the positively charged nitrogen atom of the tricyclic unit of the compounds of formula (I). This counterion may be a halide (such as a chloride, bromide, iodide), a sulphate, a methosulphate, a phosphate and a tosylate.

The expression "heteroatom" is understood to mean, as used herein, an atom other than a carbon atom, such as an oxygen, nitrogen or sulfur atom.

In one embodiment, $R^3$ is chosen from mono- and polycyclic radicals comprising from 5 to 100 carbon atoms, optionally aromatic, optionally comprising at least one heteroatom and optionally at least one unsaturation, it being possible for the mono- and polycyclic group to be substituted with at least one entity chosen from hydroxyl radicals, cyano radicals, halogens, amino radicals, and alkoxy and alkyl radicals comprising from 1 to 4 carbon atoms, with the proviso that $R^3$ is not an aryl group when q is equal to 0.

In one embodiment of the present disclosure, $R^3$ is chosen from heterocyclic radicals.

The expression "heterocyclic radical" is understood to mean, as used herein, a system comprising at least one 5-, 6- or 7-membered aromatic or nonaromatic ring, and from 1 to 3 heteroatoms chosen from nitrogen, sulphur and oxygen atoms, optionally fused with other rings, for example, aromatic rings, such as a phenylring, optionally comprising at least one heteroatom. These heterocycles may be additionally quaternized by an alkyl or alkylene radical. For example, in another embodiment of the present disclosure, $R^3$ is a quaternized heterocycle attached to Z by a heteroatom.

Among the heterocycles that may be used as disclosed herein, non-limiting mention may be made of, for example, pyridine, pyrazole, pyrimidine, imidazole, triazole, thiazole, pyrrole, pyrrolidine, benzothiazole, thiophene, benzimidazole, benzothiophene, benzotriazole, pyrazolopyridine and pyrazolopyrimidine radicals.

As disclosed herein, X and Y, which may be identical or different, are chosen from nitrogen atoms and CR' radicals wherein R' is chosen from a hydrogen atom and alkyl radicals comprising 1 to 6 carbon atoms. In still another embodiment of the present disclosure, X and Y are each a nitrogen atom.

As disclosed herein, $R^6$ is chosen from mono- and polycyclic radicals comprising from 5 to 100 carbon atoms and optionally at least one heteroatom and optionally at least one unsaturation, it being possible for the mono- and polycyclic radicals to be substituted. In yet another embodiment of the present disclosure, $R^6$ is chosen from aryl radicals comprising from 6 to 18 carbon atoms, optionally substituted with at least one entity chosen from hydroxyl radicals, cyano radicals, halogens, amino radicals, aryl radicals, alkoxy radicals and alkyl radicals comprising from 1 to 4 carbon atoms. By way of non-limiting example, $R^6$ may be a phenol group.

For the compounds of formula (I), the subscript p may be equal to 0 or 1. In one embodiment of the present disclosure, p is equal to 0. When p is equal to 0, Z is a single bond and the compounds of formula (I) correspond to the following formula:

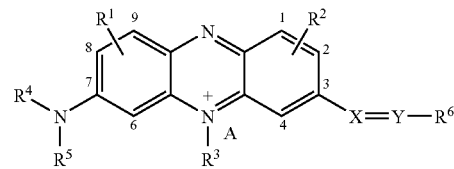

wherein:

$R^3$ is chosen from mono- and polycyclic radicals as defined above, with the exclusion of aryl groups.

When p is equal to 1, the compounds of formula (I) correspond to the following formula:

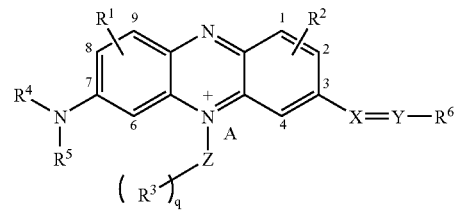

wherein:

Z is chosen from alkylene radicals as defined above, the alkylene radical being substituted with one to five $R^3$ radicals, it being possible for the $R^3$ radicals to be identical or different when q is greater than or equal to 2.

According to another embodiment of the present disclosure, when p is equal to 1, q is equal to 1, that is to say that Z is substituted with an $R^3$ radical.

As an example of compounds of formula (I) that can be used in the context of the present disclosure, non-limiting mention may be made of the compound of formula (II):

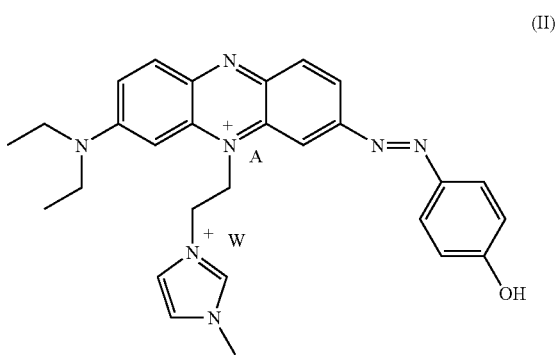

(II)

wherein A and W, which may be identical or different, are chosen from anionic counterions, as defined above, for example, chloride ions.

These dyes may be obtained by conventional synthesis schemes such as those described in French Patent Application FR 1,285,848.

The compounds of formula (I) may be defined as direct dyes, i.e., they do not require developing with an oxidizing agent like oxidation dyes do.

The dyes of the present disclosure can make it possible to obtain intense dyeing on natural or optionally sensitised, for example, chemically treated, hair.

The dyes disclosed herein also make it possible to obtain varying glints which may be chromatic or dark, very intense, not very selective and/or exhibit good fastness.

For example, the dyes of the present disclosure make it possible to obtain neutral grey and black glints which change little over time.

The at least one dye of formula (I) can be present in the dyeing composition in an amount ranging from 0.001 to 20% by weight, relative to the total weight of the dyeing composition, for instance from 0.01 to 10% by weight, such as from 0.1 to 5%.

The dyeing composition according to the present disclosure, for example, comprises an aqueous medium that comprises water or a mixture of water and at least one cosmetically acceptable organic solvent. There may be mentioned, by way of non-limiting examples of cosmetically acceptable organic solvents, alcohols such as ethyl alcohol, isopropyl alcohol, benzyl alcohol, polyols, polyol ethers, alkanes, ketones and mixtures thereof.

In addition, the dyeing composition may comprise at least one direct dye different from the compounds of formula (I). These direct dyes may be chosen from the direct dyes conventionally used in direct dyeing. Non-limiting mention may be made, among these dyes, commonly used aromatic and/or nonaromatic dyes such as nitro dyes, methines, azomethines, styriles, triarylmethanes, diarylmethanes, azo dyes, anthraquinone and naphthoquinone dyes, porphyrins, tetraphenylporphyrins, metalloporphyrins, phthalocyanines, natural dyes of the carotenoid, terpenoid and flavonoid type, fluorescent dyes such as fluorescein, rhodamine and coumarin.

The composition of the present disclosure may additionally comprise at least one oxidation base optionally combined with at least one coupler conventionally used for oxidation dyeing.

By way of examples of oxidation bases, non-limiting mention may be made of para-phenylenediamines, bisphenylalkylenediamines, para-aminophenols, ortho-aminophenols, and heterocyclic bases such as diaminopyrazoles.

The at least one coupler that may be combined with the at least one oxidation base may include meta-phenylenediamine couplers, meta-aminophenol couplers, meta-diphenol couplers, naphthalenic couplers and heterocyclic couplers.

In addition to the dyes, the dyeing composition of the present disclosure may also comprise at least one customary additive for dyeing compositions, it being possible for these additives to be chosen from surfactants, thickening agents, antioxidants, sequestering agents, dispersing agents, hair conditioners, preservatives, opacifying agents and perfumes.

It is understood that persons skilled in the art will make an appropriate choice of these additives so that the beneficial properties of the claimed composition comprising at least one compound of formula (I) as defined above are not impaired by the abovementioned additives.

The at least one surfactant that may be present in the composition may be chosen from anionic, nonionic, amphoteric and cationic surfactants. Anionic, nonionic, amphoteric and cationic surfactants that are suitable for use as disclosed herein include, for example, the following:

Anionic Surfactants

By way of examples of anionic surfactants which can be used, alone or as mixtures, non-limiting mention may be made of salts, for instance, alkali metal salts (sodium salts, magnesium salts, ammonium salts, amine salts, amino alcohol salts and the like) of the following compounds: alkyl sulphates, alkyl ether sulphates, alkyl amidoether sulphates, alkyl aryl polyether sulphates, monoglyceride sulphates; alkyl sulphonates, alkyl phosphates, alkyl amide sulphonates, alkyl aryl sulphonates, α-olefin sulphonates, paraffin sulphonates; $(C_6-C_{24})$alkyl sulphosuccinates, $(C_6-C_{24})$alkyl ether sulphosuccinates, $(C_6-C_{24})$alkyl amide sulphosuccinates, $(C_6-C_{24})$alkyl sulphoacetates; $(C_6-C_{24})$acyl sarcosinates and $(C_6-C_{24})$acyl glutamates.

Non-limiting mention may also be made of $(C_6-C_{24})$alkyl polyglycoside carboxylic esters such as alkyl polyglucoside citrates, alkyl polyglucoside tartrates, alkyl polyglucoside sulphosuccinates and alkyl polyglucoside sulphosuccinamates; acyl isethionates and N-acyltaurates, the alkyl and acyl radicals of all these compounds, for instance comprising from 12 to 20 carbon atoms, and the aryl radical for example, may be chosen from phenyl and benzyl radicals.

Further non-limiting mention may also be made of the salts of fatty acids such as the salts of oleic, ricinoleic, palmitic and stearic acids, acids of copra oil or of hydrogenated copra oil; acyl lactylates whose acyl radical comprises from 8 to 20 carbon atoms; alkyl D-galactoside uronic acids and their salts; polyoxyalkylenated $(C_6-C_{24})$alkyl ether carboxylic acids, polyoxyalkylenated $(C_6-C_{24})$alkyl amidoether carboxylic acids and their salts, for example, those comprising from 2 to 50 alkylene oxide, such as ethylene oxide, groups and mixtures thereof.

Nonionic Surfactants

Nonionic surfactants useful herein are compounds which are well known per se (see for example the "Handbook of Surfactants", M. R. PORTER, Ed. Blackie & Son, Glasgow and London, 1991, 116–178.

Thus, used alone or as mixtures, non-limiting mention may be made of nonionic surfactants chosen, for example, from alcohols, α-diols, polyethoxylated and polypropoxylated alkylphenols having a fatty chain comprising for example from 8 to 18 carbon atoms, it being possible for the number of ethylene oxide or propylene oxide groups to be for instance, from 2 to 50; copolymers of ethylene oxide and propylene oxide, condensates of ethylene oxide and propylene oxide with fatty alcohols, polyethoxylated fatty amides, for example, having from 2 to 30 mol of ethylene oxide; polyglycerolated fatty amides comprising on average from 1 to 5, such as from 1.5 to 4, glycerol groups; oxyethylenated fatty acid esters of sorbitan comprising from 2 to 30 mol of ethylene oxide; fatty acid esters of sucrose, fatty acid esters of polyethylene glycol; alkyl polyglycosides; derivatives of N-alkyl glucamine and amine oxides such as ($C_{10}$–$C_{14}$)alkyl amine oxides or N-acylaminopropylmorpholine oxides.

Amphoteric Surfactants

Among the amphoteric (or zwitterionic) surfactants, non-limiting mention may be made of those chosen, for example, alone or as mixtures, from the derivatives of aliphatic secondary or tertiary amines whose aliphatic radical is a linear or branched chain comprising from 8 to 18 carbon atoms and comprising at least one water-solubilizing anionic group, for example a carboxylate, a sulphonate, a sulphate, a phosphate or a phosphonate.

Further non-limiting mention may also be made of ($C_8$–$C_{20}$)alkyl betaines, sulphobetaines, ($C_8$–$C_{20}$)alkyl amido($C_1$–$C_6$)alkyl betaines and ($C_8$–$C_{20}$)alkyl amido ($C_1$–$C_6$)alkyl sulphobetaines.

Among the amine derivatives, non-limiting mention may be made, for example, of the compounds marketed by the company Rhodia Chimie under the trade name Miranol®, which are described in U.S. Pat. Nos. 2,528,378 and 2,781,354, and which are classified in the CTFA Dictionary, 5$^{th}$ edition, 1993, under the names "disodium cocoamphodiacetate", "disodium lauroamphodiacetate", "disodium caprylamphodiacetate", "disodium capryloamphodiacetate", "disodium cocoamphodipropionate", "disodium lauroamphodipropionate", "disodium caprylamphodipropionate", "disodium capryloamphodipropionate", "lauroamphodipropionic acid" and "cocoamphodipropionic acid".

Cationic Surfactants

Among the cationic surfactants which may be used alone or as mixtures, non-limiting mention may be made of the salts of optionally polyoxyalkylenated primary, secondary and tertiary fatty amines; quaternary ammonium salts such as tetraalkylammonium, alkylamidoalkyltrialkylammonium, trialkylbenzylammonium, trialkylhydroxyalkylammonium and alkylpyridinium chlorides and bromides; imidazoline derivatives and amine oxides having a cationic character.

The thickening agents which may be incorporated into the compositions of the invention may be of inorganic or organic origin. Among these, non-limiting mention may be made of thickening polymers of natural origin such as gums (xanthan gum, carob gum, guar gum), thickening polymers of synthetic origin (such as hydroxyethylcellulose, polyacrylic acids). Among these synthetic polymers, further non-limiting mention may be made, for example, of associative polymers comprising a fatty chain, such as associative polymers of the acrylic or polyurethane type.

The pH of the dyeing composition in accordance with the present disclosure ranges from 3 to 12, such as from 5 to 11, for instance from 6 to 10.

The pH may be adjusted to the desired value by virtue of the addition to the composition of acidifying or alkalinizing agents that aregenerally used in dyeing keratinous fibers, or alternatively with the aid of conventional buffer systems.

Among the acidifying agents that may be used, non-limiting mention may be made of, by way of example, inorganic or organic acids such as hydrochloric acid, orthophosphoric acid, sulphuric acid, carboxylic acids such as acetic acid, tartaric acid, citric acid, lactic acid, and sulphonic acids.

Among the alkalinizing agents that may be used, non-limiting mention may be made of, by way of example, aqueous ammonia, alkali metal carbonates, alkanolamines such as mono-, di- and triethanolamines and derivatives thereof, sodium or potassium hydroxides and compounds of the following formula (III):

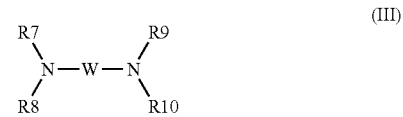

wherein

W is a propylene residue optionally substituted with a radical chosen from hydroxyl radicals and $C_1$–$C_4$ alkyl radicals;

$R_7$, $R_8$, $R_9$ and $R_{10}$, which may be identical or different, are chosen from hydrogen atoms, $C_1$–$C_4$ alkyl radicals and $C_1$–$C_4$ hydroxyalkyl radicals.

The cosmetic composition may be provided in various forms such as a lotion, a cream, a gel or any other appropriate form for dyeing keratinous fibers. It may also be packaged under pressure in an aerosol can in the presence of a propellant, and can also form a mousse.

The present disclosure also relates to the use of compounds of formula (I) as defined above, as a direct dye in compositions for dyeing keratinous fibers, for instance human keratinous fibers, such as the hair.

Finally, the present disclosure also relates to a process for the direct dyeing of keratinous fibers, comprising the following:

applying to the keratinous fibers a dyeing composition as defined above;

leaving the composition on the keratinous fibers for a sufficient leave-in time to obtain a desired color;

optionally rinsing the keratinous fibers so as to remove the said dyeing composition therefrom;

optionally washing the keratinous fibers once or several times, rinsing them after each wash; and drying the keratinous fibers.

Thus, the direct dyeing process of the present disclosure comprises a applying to the hair to be dyed the dyeing composition as defined above, and then, leaving the composition on and in the fibers, for a leave-in time ranging from 3 to 60 minutes, for instance from 5 to 40 minutes, such as from 15 to 30 minutes, so as to give the composition time to properly act on the hair. This leave-in phase may be optionally carried out at a temperature ranging from room temperature to 80° C., such as from 25 to 55° C.

The keratinous fibers thus dyed are optionally rinsed in order to remove the dyeing composition that has reacted with the fibers and optionally washed once or several times.

When the dyeing composition comprises at least one compound of formula (I) and at least one oxidation dye, as discussed above, the dyeing process requires additionally developing, with at least one oxidizing agent, the color of the oxidation dye.

Consequently, the present disclosure also relates to a method for dyeing keratinous fibers comprising:

applying to the keratinous fibers a dyeing composition comprising at least one compound of formula (I) as defined above and at least one oxidation dye, the color of the oxidation dye being developed with at least one oxidizing agent;

leaving the composition on and in the keratinous fibers for a sufficient leave-in time to obtain a desired color;

optionally rinsing the keratinous fibers in order to remove the said dyeing composition therefrom;

optionally washing the keratinous fibers once or several times, rinsing them after each wash; and drying the said keratinous fibers.

The oxidizing agents which may be used may be chosen from, for example, hydrogen peroxide, urea peroxide, alkali metal bromates, persalts such as perborates and persulphates, peracids and oxidase enzymes such as peroxidases, oxidoreductases comprising two electrons such as uricases, and oxygenases comprising four electrons such as laccases. In one embodiment of the present disclosure, the oxidizing agent is hydrogen peroxide.

The at least one oxidizing agent may be added to the composition of the present disclosure just at the time of use or it may be part of an oxidizing composition comprising it.

The composition is left in, for a period of time ranging from 3 to 60 minutes, for instance from 5 to 40 minutes, such as from 15 to 30 minutes, so as to give the composition enough time to properly act on the hair and for the development to take place. This leave-in phase may be carried out at a temperature ranging from room temperature to 80° C., such as from 25 to 55° C.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the present disclosure are approximations, the numerical values set forth in the specific examples are reported as precisely as possible. Any numerical value, however, inherently contain certain errors necessarily resulting from the standard deviation found in their respective testing measurements.

The following example is intended to illustrate the present disclosure in a non-limiting manner.

EXAMPLE

A dyeing composition 1 in accordance with the present disclosure having the constituents described in Table 1 below is prepared. This composition comprises a dye (1) (molecular weight: 518 g/mol) in accordance with the present disclosure, corresponding to the following formula:

TABLE 1

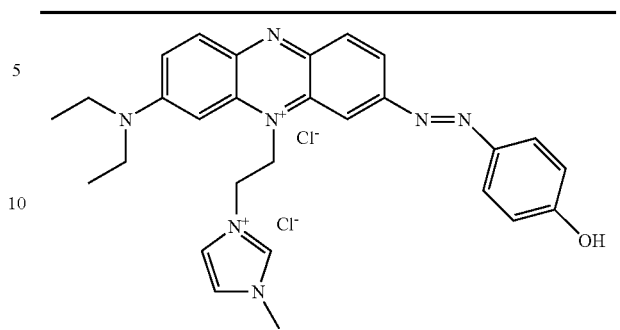

| Constituent | Quantity |
| --- | --- |
| Dye (1) | 0.52 g |
| Benzyl alcohol | 4 g |
| Polyethylene glycol 6 EO | 6 g |
| Hydroxyethylcellulose | 0.7 g |
| Alkyl polyglucoside as an aqueous solution containing 60% AM* | 4.5 g AM* |
| Phosphate buffer | qs pH 7 |
| Demineralized water | qs 100 g |

*AM: Active material.

What is claimed is:

1. A composition for dyeing keratinous fibers comprising at least one direct dye of formula (I):

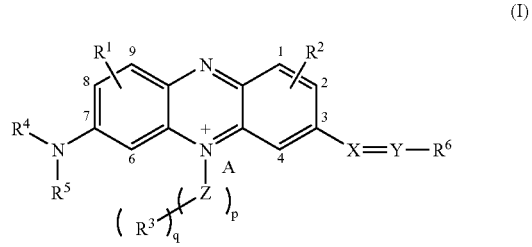

(I)

wherein:
R$^1$ and R$^2$, which may be identical or different, are chosen from:
hydrogen atoms;
alkyl radicals comprising from 1 to 6 carbon atoms, it being possible for the alkyl radicals to be optionally substituted with at least one entity chosen from hydroxyl radicals, amino radicals, halogens, aryl radicals, and alkoxy radicals comprising from 1 to 3 carbon atoms;
aryl radicals comprising from 6 to 18 carbon atoms, it being possible for the aryl radicals to be optionally substituted with at least one radical chosen from amino radicals, hydroxyl radicals, alkoxy radicals comprising from 1 to 3 carbon atoms, and alkyl radicals comprising from 1 to 6 carbon atoms;
carboxyalkyl radicals comprising from 1 to 6 carbon atoms; and
sulphoalkyl radicals comprising from 1 to 6 carbon atoms;
p is equal to 0 or 1;
when p is equal to 0, q is equal to 1, and Z is a single bond;
when p is equal to 1, Z is chosen from alkylene radicals comprising from 1 to 4 carbon atoms, the alkylene radicals being substituted with q $R^3$ radicals, which may be identical or different, wherein q is an integer ranging from 1 to 5;

$R^3$ is chosen from mono- and polycyclic radicals comprising from 5 to 100 carbon atoms, which are optionally aromatic, optionally comprising at least one heteroatom and optionally at least one unsaturation, it being possible for the mono and polycyclic radicals to be substituted with at least one entity chosen from hydroxyl radicals, cyano radicals, halogens, amino radicals, alkoxy radicals and alkyl radicals comprising from 1 to 4 carbon atoms, with the proviso that when p is equal to 0, $R^3$ is not an aryl radical;

$R^6$ is chosen from mono- and polycyclic radicals comprising from 5 to 100 carbon atoms, and optionally at least one heteroatom and optionally at least one unsaturation, it being possible for the mono- and polycyclic radicals to be substituted with at least one entity chosen from hydroxyl radicals, cyano radicals, halogens, aminoradicals, aryl radicals, alkoxy radicals and alkyl radicals comprising from 1 to 4 carbon atoms;

$R^4$ and $R^5$, which may be identical or different, are chosen from hydrogen atoms, aryl radicals and alkyl radicals comprising from 1 to 6 carbon atoms, the radicals being optionally substituted with at least one entity chosen from hydroxyl radicals, cyano radicals, halogens, amino radicals, aryl radicals, and alkoxy radicals comprising from 1 to 4 carbon atoms;

X and Y, which may be identical or different, are chosen from nitrogen atoms and CR' radicals wherein R' is chosen from a hydrogen atom and alkyl radicals comprising from 1 to 6 carbon atoms; and A is an anionic counterion.

2. The dyeing composition according to claim 1, wherein, when p is equal to 1, q is equal to 1.

3. The dyeing composition according to claim 1, wherein $R^3$ is chosen from aromatic heterocycles.

4. The dyeing composition according to claim 3, wherein the aromatic heterocycle is chosen from pyridine, pyrazole, pyrimidine, imidazole, triazole, thiazole, pyrrole, pyrrolidine, benzothiazole, thiophene, benzimidazole, benzothiophene, benzotriazole, pyrazolopyridine and pyrazolopyrimidine radicals.

5. The dyeing composition according to claim 1, wherein X and Y are each a nitrogen atom.

6. The dyeing composition according to claim 1, wherein $R^6$ is chosen from aryl radicals comprising from 6 to 18 carbon atoms, optionally substituted with at least one entity chosen from hydroxyl radicals, cyano radicals, halogens, amino radicals, aryl radicals, alkoxy radicals and alkyl radicals comprising from 1 to 4 carbon atoms.

7. The dyeing composition according to claim 6, wherein $R^6$ is a phenol group.

8. The dyeing composition according to claim 1, wherein the at least one direct dye of formula (I) is a compound of formula (II):

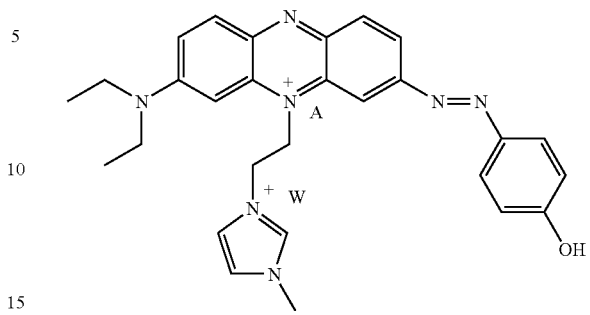

wherein A and W, which may be identical or different, are chosen from anionic counterions.

9. The dyeing composition according to claim 1, wherein the at least one direct dye of formula (I) is present in an amount ranging from 0.001% to 20% by weight, relative to the total weight of the composition.

10. The dyeing composition according to claim 9, wherein the at least one direct dye of formula (I) is present in an amount ranging from 0.01% to 10% by weight, relative to the total weight of the composition.

11. The dyeing composition according to claim 10, wherein the at least one direct dye of formula (I) is present in an amount ranging from 0.1% to 5% by weight, relative to the total weight of the composition.

12. The dyeing composition according to claim 1, comprising an aqueous medium chosen from water and a mixture of water and at least one cosmetically acceptable organic solvent.

13. The dyeing composition according to claim 12, wherein the at least one cosmetically acceptable organic solvent is chosen from alcohols, polyol ethers, alkanes, and ketones.

14. The dyeing composition according to claim 13, wherein the at least one alcohol is chosen from ethyl alcohol, isopropyl alcohol, benzyl alcohol, and polyols.

15. The dyeing composition according to claim 1, further comprising at least one direct dye different from the direct dyes of formula (I).

16. The dyeing composition according to claim 15, wherein the at least one direct dye different from the direct dyes of formula (I) is chosen from nitro dyes, methines, azomethines, styriles, triarylmethanes, diarylmethanes, azo dyes, anthraquinone dyes, naphthoquinone dyes, porphyrins, tetraphenylporphyrins, metalloporphyrins, phthalocyanines, natural dyes of the carotenoid, terpenoid and flavonoid type, and fluorescent dyes.

17. The dyeing composition according to claim 16, wherein the fluorescent dyes are chosen from fluorescein, rhodamine and coumarin.

18. The dyeing composition according to claim 1, further comprising at least one oxidation base optionally combined with at least one coupler.

19. The dyeing composition according to claim 18, wherein the at least one oxidation base is chosen from para-phenylenediamines, bisphenylalkylenediamines, para-aminophenols, ortho-aminophenols and heterocyclic bases.

20. The dyeing composition according to claim 18, wherein the at least one coupler is chosen from meta-phenylenediamine couplers, meta-aminophenol couplers, meta-diphenol couplers, naphthalenic couplers and heterocyclic couplers.

21. The dyeing composition according to claim 1, further comprising at least one additive chosen from surfactants, thickening agents, antioxidants, sequestering agents, dispersing agents, hair conditioners, preservatives, opacifying agents, alkalinizing agents, acidifying agents and perfumes.

22. The dyeing composition according to claim 1, wherein the pH of the composition ranges from 3 to 12.

23. The dyeing composition according to claim 22, wherein the pH of the composition ranges from 5 to 11.

24. The dyeing composition according to claim 23, wherein the pH of the composition ranges from 6 to 10.

25. A process for the direct dyeing of keratinous fibers, comprising:
applying to the keratinous fibers a dyeing composition comprising at least one direct dye of formula (I):

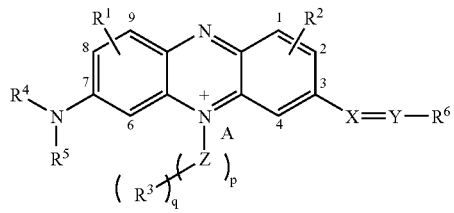

(I)

wherein:
$R^1$ and $R^2$, which may be identical or different, are chosen from:
hydrogen atoms;
alkyl radicals comprising from 1 to 6 carbon atoms, it being possible for the alkyl radicals to be optionally substituted with at least one entity chosen from hydroxyl radicals, amino radicals, halogens, aryl radicals, and alkoxy radicals comprising from 1 to 3 carbon atoms;
aryl radicals comprising from 6 to 18 carbon atoms, it being possible for the aryl radicals to be optionally substituted with at least one radical chosen from amino radicals, hydroxyl radicals, alkoxy radicals comprising from 1 to 3 carbon atoms, and alkyl radicals comprising from 1 to 6 carbon atoms;
carboxyalkyl radicals comprising from 1 to 6 carbon atoms; and
sulphoalkyl radicals comprising from 1 to 6 carbon atoms;
p is equal to 0 or 1;
when p is equal to 0, q is equal to 1, and Z is a single bond;
when p is equal to 1, Z is chosen from alkylene radicals comprising from 1 to 4 carbon atoms, the alkylene radicals being substituted with q $R^3$ radicals, which may be identical or different, wherein q is an integer ranging from 1 to 5;
$R^3$ is chosen from mono- and polycyclic radicals comprising from 5 to 100 carbon atoms, which are optionally aromatic, optionally comprising at least one heteroatom and optionally at least one unsaturation, it being possible for the mono and polycyclic radicals to be substituted with at least one entity chosen from hydroxyl radicals, cyano radicals, halogens, amino radicals, alkoxy radicals and alkyl radicals comprising from 1 to 4 carbon atoms, with the proviso that when p is equal to 0, $R^3$ is not an aryl radical;
$R^6$ is chosen from mono- and polycyclic radicals comprising from 5 to 100 carbon atoms, and optionally at least one heteroatom and optionally at least one unsaturation, it being possible for the mono- and polycyclic radicals to be substituted with at least one entity chosen from hydroxyl radicals, cyano radicals, halogens, amino radicals, aryl radicals, alkoxy radicals and alkyl radicals comprising from 1 to 4 carbon atoms;
$R^4$ and $R^5$, which may be identical or different, are chosen from hydrogen atoms, aryl radicals and alkyl radicals comprising from 1 to 6 carbon atoms, the radicals being optionally substituted with at least one entity chosen from hydroxyl radicals, cyano radicals, halogens, amino radicals, aryl radicals, and alkoxy radicals comprising from 1 to 4 carbon atoms;
X and Y, which may be identical or different, are chosen from nitrogen atoms and CR' radicals wherein R' is chosen from a hydrogen atom and alkyl radicals comprising from 1 to 6 carbon atoms; and
A is an anionic counterion;
leaving the composition on the keratinous fibers for a sufficient time to obtain a desired color;
optionally rinsing the keratinous fibers so as to remove the dyeing composition therefrom;
optionally washing the keratinous fibers once or several times, rinsing them after each wash; and
drying the keratinous fibers.

26. A process for dyeing keratinous fibers comprising:
applying to the keratinous fibers a dyeing composition comprising
at least one oxidation dye, wherein the color of the oxidation dye is developed with at least one oxidizing agent, and
at least one direct dye of formula (I):

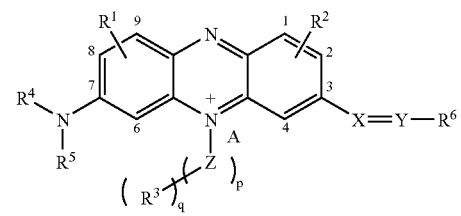

(I)

wherein:
$R^1$ and $R^2$, which may be identical or different, are chosen from:
hydrogen atoms;
alkyl radicals comprising from 1 to 6 carbon atoms, it being possible for the alkyl radicals to be optionally substituted with at least one entity chosen from hydroxyl radicals, amino radicals, halogens, aryl radicals, and alkoxy radicals comprising from 1 to 3 carbon atoms;
aryl radicals comprising from 6 to 18 carbon atoms, it being possible for the aryl radicals to be optionally substituted with at least one radical chosen from amino radicals, hydroxyl radicals, alkoxy radicals comprising from 1 to 3 carbon atoms, and alkyl radicals comprising from 1 to 6 carbon atoms;

carboxyalkyl radicals comprising from 1 to 6 carbon atoms; and sulphoalkyl radicals comprising from 1 to 6 carbon atoms;

p is equal to 0 or 1;

when p is equal to 0, q is equal to 1, and Z is a single bond;

when p is equal to 1, Z is chosen from alkylene radicals comprising from 1 to 4 carbon atoms, the alkylene radicals being substituted with q $R^3$ radicals, which may be identical or different, wherein q is an integer ranging from 1 to 5;

$R^3$ is chosen from mono- and polycyclic radicals comprising from 5 to 100 carbon atoms, which are optionally aromatic, optionally comprising at least one heteroatom and optionally at least one unsaturation, it being possible for the mono and polycyclic radicals to be substituted with at least one entity chosen from hydroxyl radicals, cyano radicals, halogens, amino radicals, alkoxy radicals and alkyl radicals comprising from 1 to 4 carbon atoms, with the proviso that when p is equal to 0, $R^3$ is not an aryl radical;

$R^6$ is chosen from mono- and polycyclic radicals comprising from 5 to 100 carbon atoms, and optionally at least one heteroatom and optionally at least one unsaturation, it being possible for the mono- and polycyclic radicals to be substituted with at least one entity chosen from hydroxyl radicals, cyano radicals, halogens, aminoradicals, aryl radicals, alkoxy radicals and alkyl radicals comprising from 1 to 4 carbon atoms;

$R^4$ and $R^5$, which may be identical or different, are chosen from hydrogen atoms, aryl radicals and alkyl radicals comprising from 1 to 6 carbon atoms, the radicals being optionally substituted with at least one entity chosen from hydroxyl radicals, cyano radicals, halogens, amino radicals, aryl radicals, and alkoxy radicals comprising from 1 to 4 carbon atoms;

X and Y, which may be identical or different, are chosen from nitrogen atoms and CR' radicals wherein R' is chosen from a hydrogen atom and alkyl radicals comprising from 1 to 6 carbon atoms; and A is an anionic counterion;

leaving the dyeing composition on the keratinous fibers for a sufficient time to obtain a desired color;

optionally rinsing the keratinous fibers in order to remove the dyeing composition therefrom;

optionally washing the keratinous fibers once or several times, rinsing them after each wash; and drying the keratinous fibers.

27. The process according to claim 25, wherein the leave-in time ranges from 3 to 60 minutes.

28. The process according to claim 27, wherein the leave-in time ranges from 5 to 40 minutes.

29. The process according to claim 28, wherein the leave-in time ranges from 15 to 30 minutes.

30. The process according to claim 26, wherein the at least one oxidizing agent is chosen from hydrogen peroxide, urea peroxide, alkali metal bromates, persalts, peracids, oxidase enzymes, oxidoreductases comprising two electrons, and oxygenases comprising four electrons.

31. The process according to claim 30, wherein the at least one persalt is chosen from perborates and persulphates.

32. The process according to claim 30, wherein the at least one oxidase enzyme is chosen from peroxidases.

33. The process according to claim 30, wherein the at least one oxidoreductase comprising two electrons is chosen from uricases.

34. The process according to claim 30, wherein the at least one oxygenase comprising four electrons is chosen from laccases.

* * * * *